United States Patent
Markman

[11] Patent Number: 5,643,308
[45] Date of Patent: Jul. 1, 1997

[54] METHOD AND APPARATUS FOR FORMING MULTIPLE CAVITIES FOR PLACEMENT OF HAIR GRAFTS

[76] Inventor: Barry Stephen Markman, 5157 Jarom, Las Vegas, Nev. 89120

[21] Appl. No.: 395,455

[22] Filed: Feb. 28, 1995

[51] Int. Cl.⁶ .................................................. A61B 17/00
[52] U.S. Cl. ........................... 606/187; 623/15; 606/1
[58] Field of Search .......................... 606/1, 186, 187; 623/15; 604/173

[56] References Cited

U.S. PATENT DOCUMENTS

| | | |
|---|---|---|
| 2,636,460 | 4/1953 | Seiderman . |
| 3,003,155 | 10/1961 | Meilzynski et al. . |
| 3,513,860 | 5/1970 | Kost . |
| 3,514,791 | 6/1970 | Sparks . |
| 3,596,292 | 8/1971 | Erb et al. . |
| 3,694,819 | 10/1972 | Meyer . |
| 3,699,969 | 10/1972 | Allen . |
| 3,811,425 | 5/1974 | Widdifield . |
| 3,831,202 | 8/1974 | Hulsen . |
| 4,150,669 | 4/1979 | Latorre . |
| 4,167,179 | 9/1979 | Kirsch . |
| 4,476,864 | 10/1984 | Tezel . |
| 4,586,490 | 5/1986 | Katz . |
| 4,695,273 | 9/1987 | Brown . |
| 5,417,683 | 5/1995 | Shiao . |

FOREIGN PATENT DOCUMENTS

| | | |
|---|---|---|
| 1595597 | 7/1970 | France . |
| 1267784 | 5/1968 | Germany . |
| 2809327 | 4/1979 | Germany . |

*Primary Examiner*—Michael Buiz
*Assistant Examiner*—William Lewis
*Attorney, Agent, or Firm*—Quirk & Tratos

[57] ABSTRACT

A method and apparatus for forming multiple cavities in the tissue of a patient into which hair transplant grafts are placed is disclosed. In one form, the apparatus is a cartridge comprising a housing, a guide, and a depressor. The guide comprises a plurality of dilator accepting passages located in the housing or in a template in the housing. The depressor is a plate or actuated plunger located at a first end of the dilators which, when depressed, forces the dilators from the guide into tissue of a patient. In a second form, the apparatus comprises mating male and female templates. The male template includes a number of downwardly extending spikes for engagement with a number of downwardly extending hollow guides on the female template. The spikes of the engaging male and female templates are pressed into the tissue and the male template is removed, leaving cavities formed by the hollow guides of the female template, into which hair grafts are located.

39 Claims, 4 Drawing Sheets

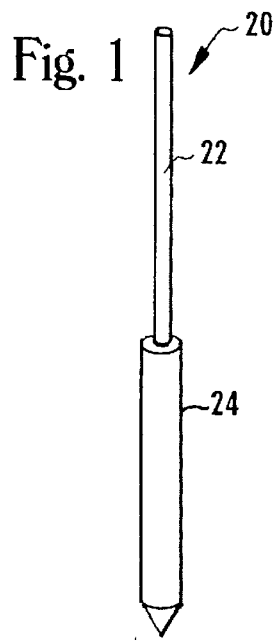
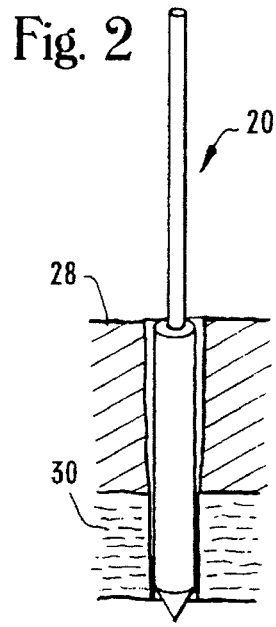
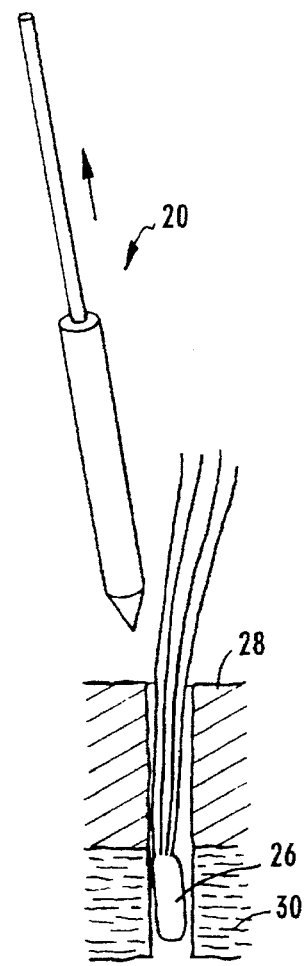
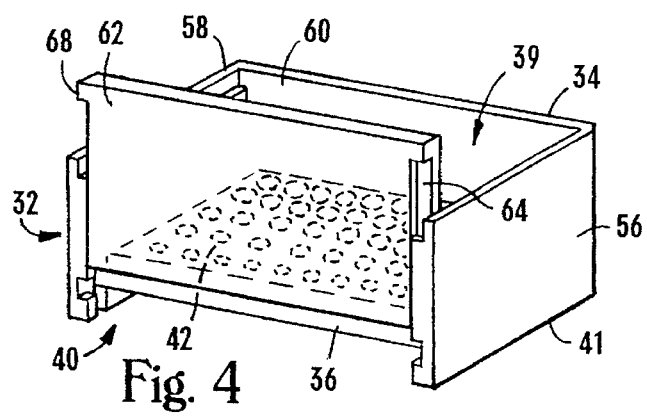
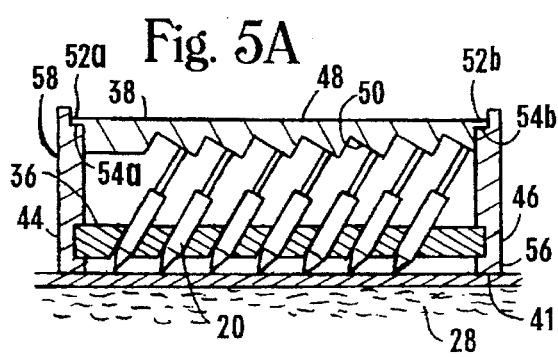
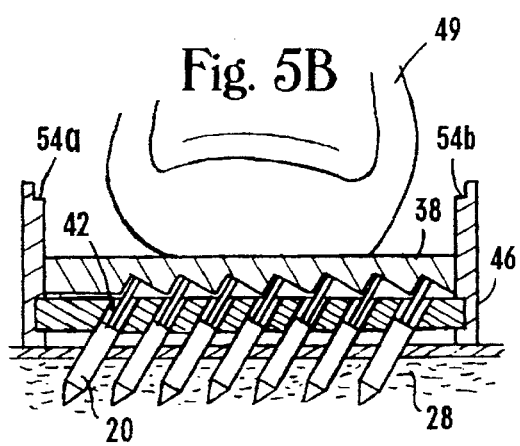

METHOD AND APPARATUS FOR FORMING MULTIPLE CAVITIES FOR PLACEMENT OF HAIR GRAFTS

FIELD OF THE INVENTION

The present invention relates to the placement of hair grafts. In particular, the invention is a method and device for forming a plurality of cavities in a predetermined pattern for positioning of hair grafts.

BACKGROUND OF THE INVENTION

Hair transplants have become commonplace over the last few years. In one of the newest technique of transplanting hair, small "grafts" of tissue containing only a few hairs are placed in sites on a recipient's scalp.

In particular, hair from other portions of the recipient are cut into very small cylindrical sections, or grafts. The recipients scalp is anesthetized, and then expanded by infusing saline into the scalp beneath the galeal layer. The surgeon inserts a needle-like dilator through the scalp, including the galeal layer, forming a cavity. The dilator is removed, and a donor graft is inserted into the cavity.

The success rate of this technique depends primarily upon whether the dilator succeeds in forming a cavity which extends below the galeal layer, and upon the time lapse between preparation and insertion of the graft.

New techniques in hair grafting require a large number, often 200 to 600, grafts to be placed during a single session. In the present technique, dilators are individually placed by hand. This is not only time consuming, but is inexact, since the surgeon places the dilators essentially randomly.

In order for the transplanted hair to have a uniform look and proper coverage, however, the grafts must be arranged on the scalp in specific patterns. For example, numerous small grafts are often placed near the hairline, while larger grafts are placed less densely on the top and rear of the scalp.

A need exists for a method of easily forming cavities into which hair grafts are inserted and for controlling their location and number across the entire scalp.

SUMMARY OF THE INVENTION

The present invention is a method and device for forming a number of cavities in the tissue of a patient into which hair grafts are inserted.

In one form of the present invention, a cartridge includes a four-sided, walled housing having open top and bottom ends. A template or guide is removably located in the housing, recessed from a bottom edge of the housing. A plurality of passageways are located through the guide for containing a plurality of dilators in a grid pattern therein.

The dilators are releasably retained in the passageways of the guide by friction between the dilators and the guide. Each dilator includes a lower or proximal probe portion for insertion into the scalp and an upper or distal grip portion by which the surgeon grasps the dilator. The distal grip portion is smaller in outer dimension than the probe portion.

The distal end of the dilators faces the top end of the housing, and the proximal end of the dilators faces the bottom end of the housing. A depressor is located over the open top end of the housing proximate the distal end of the dilators.

A surgeon places the cartridge on the patient's scalp with the bottom edge of the housing resting on the patient's head. The surgeon presses downwardly on the depressor, forcing the dilators downwardly out of the guide into the tissue of a patient. Once the dilators are inserted, the housing is removed from the scalp.

In a variation of this form of the present invention, the depressor is a plunger connected to an actuator. In this form of the invention, the housing of the cartridge is adapted to engage the triggering mechanism of an actuating mechanism, and triggering of the mechanism causes the actuator to depress the plunger, forcing the dilators from the guide into the tissue.

In other forms of the present invention, the housing is cylindrical and rotatable with respect to a base member which is adapted for insertion into a triggering mechanism. The housing includes a plurality of passages therein in which dilators are located. An actuating member passes from the base member through the housing to a plunger located proximate a first end of the dilators located in the passages. When a surgeon triggers the mechanism, one or more dilators are forced out of the passages into the tissue of a patient. The surgeon then rotates the housing with respect to the base, aligning another passage for actuation by the firing device.

In yet another form of the invention, the device for forming the cavities in the tissue comprises a female template having a number of downwardly depending guides with passages therethrough, along with a mating male template having a number of downwardly depending spikes. When engaging one another, the spikes of the male template pass through the passages in the guides of the female template, forming a single template with downwardly extending "dilators."

In use, a surgeon presses the dilators of the combined male and female templates into the tissue of a patient. The surgeon removes the male template, leaving the female template in place. The surgeon then presses a third template having downwardly extending hollow guides each containing a hair graft into the female template. The surgeon presses the spikes of the male template through the guides of the third and female templates, pressing the hair grafts downwardly. Then the surgeon removes the templates, leaving the hair grafts positioned in the tissue.

Further objects, features, and advantages of the present invention over the prior art will become apparent from the detailed description of the drawings which follows, when considered with the attached figures.

BRIEF DESCRIPTION OF THE DRAWINGS

FIG. 1 is a perspective view of a single dilator for use in the present method;

FIG. 2 is a perspective view of the dilator of FIG. 1 inserted into the scalp of a patient;

FIG. 3 is a perspective view of the dilator of FIG. 2 being removed from the scalp, and being replaced by a hair graft;

FIG. 4 is a partial perspective view of a manually operated multiple-dilator placing cartridge in accordance with the present invention; and FIG. 5a, is a front end view of the cartridge of FIG. 4 with a depressor thereof in a first, retracted position;

FIG. 5b is a front end view of the cartridge of FIG. 4 with a depressor thereof in a second, depressed position;

DETAILED DESCRIPTION OF THE PREFERRED EMBODIMENTS

Figure 6:
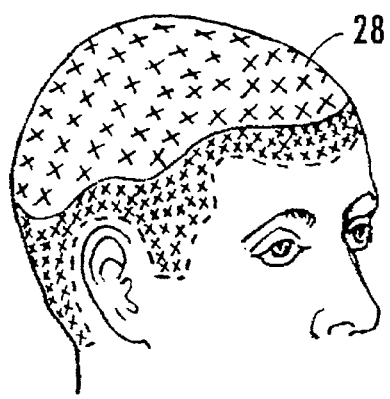
FIG. 6 is a perspective view of a patient's scalp, illustrating that certain portions of the scalp require differing hair graft sizes and densities, and thus differing sized dilators and dilator insertion points.

The present invention involves methods and devices for simultaneously forming cavities in the tissue of a patient into which hair grafts are located. In particular, the methods involve pressing dilating elements into the tissue of a patient to form cavities in which hair grafts are placed.

FIG. 1 illustrates a dilator 20 for use in some of the methods and devices of the present invention. In general, the dilator 20 comprises a distal handle portion or end 22 and a proximal probe portion or end 24. Preferably, the very end of the handle portion is blunt, and the very end of the probe portion is pointed. As illustrated in FIG. 2, the dilator 20 is inserted in the tissue of a patient, normally the scalp, for creating a cavity into which a hair graft 26 is inserted.

In a first method in accordance with the present invention, a number of dilators 20 are simultaneously located in the tissue when a surgeon manually presses on a dilator-engaging depressor 38, pushing a number of dilators through a guide 36 into the scalp, as illustrated in FIGS. 5a, and 5b.

Figure 7:
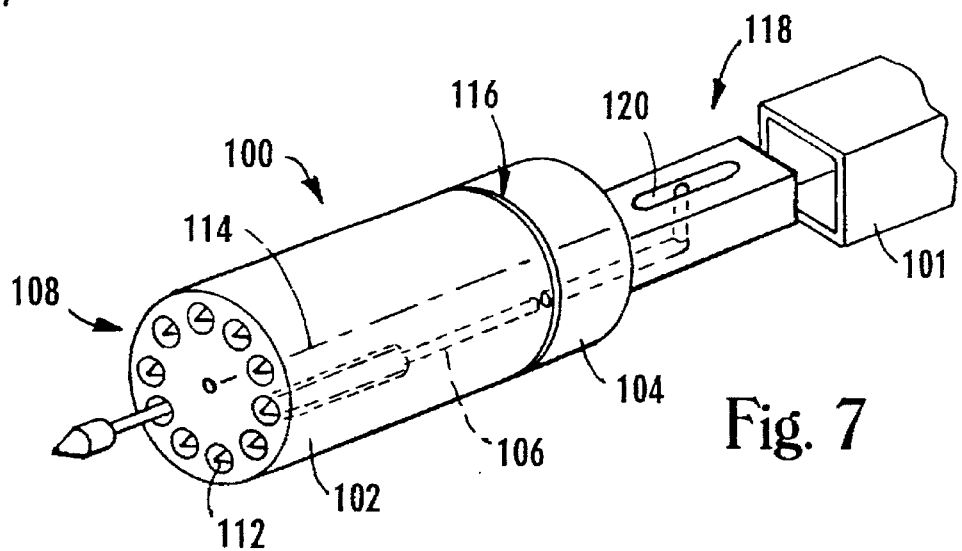
FIG. 7 is a perspective view of a second embodiment of the present invention, illustrating an automated revolving single-shot dilator cartridge.

In a second method, a series of single dilators 20 are inserted into a scalp upon actuation of a gun or other remote triggering device, via the cartridge illustrated in FIG. 7. In a third method, multiple dilators 20 are inserted into the scalp when a surgeon actuates a gun, via the cartridge illustrated in FIG. 8.

Figure 9:
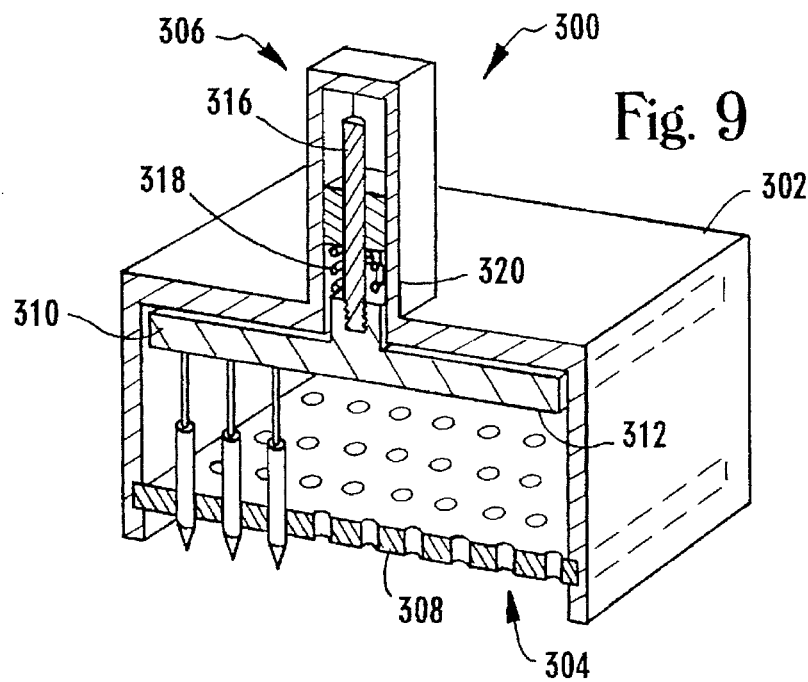
FIG. 9 is a top view of a fourth embodiment of the present invention illustrating an automatically operated dilator insertion cartridge.

In a fourth method, a number of dilators 20 are simultaneously inserted into the scalp when a surgeon triggers an actuating mechanism connected to the cartridge 300 illustrated in FIG. 9.

Figure 11:
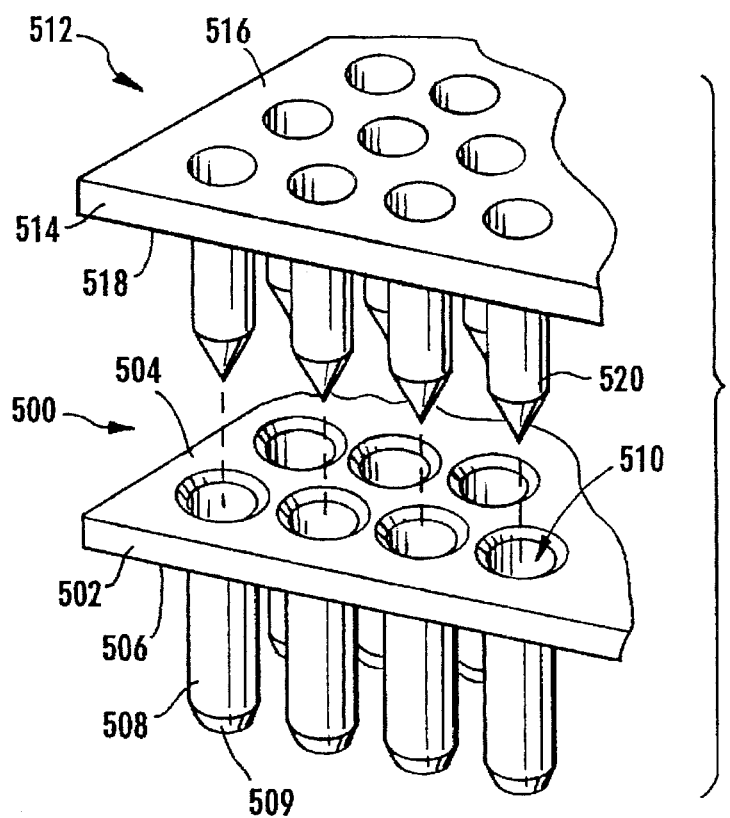
FIG. 11 is a partial perspective view of a male and a female template of a fifth form of the invention.
Figure 12:
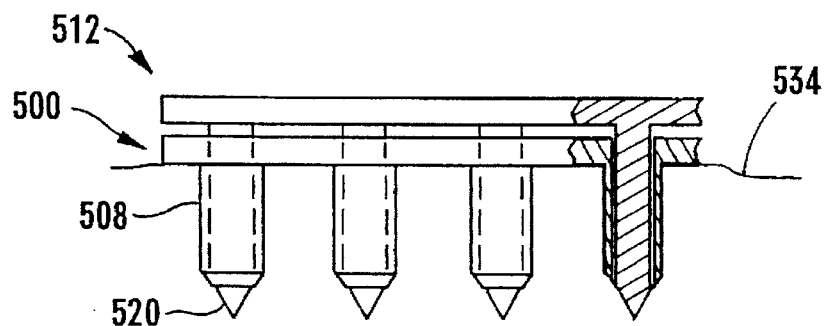
FIG. 12 is a cross-sectional side view of the male and female template of FIG. 11 shown engaging one-another and pressed into the tissue of a patient.
Figure 13:
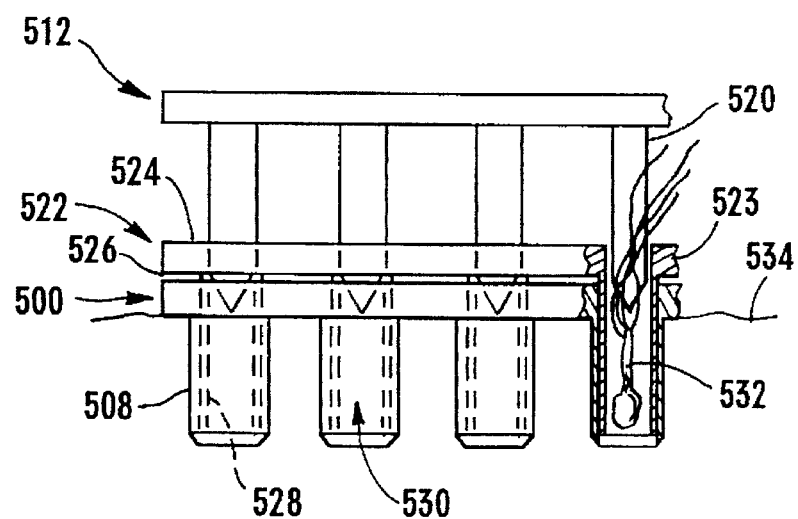
FIG. 13 is a cross-sectional side view of a third template engaging the female template of FIG. 11, with the male template engaging the third template.

In a fifth method, the interengaging templates illustrated in FIGS. 11–13, which include downwardly depending dilating spikes and guides, are used to penetrate the tissue and form open cavities into which hair grafts are inserted.

More particularly, and referring again to FIGS. 1–3, in a first form, the dilators 20 of the present invention are preferably cylindrical in shape, and about 2 cm long from end to end. In particular, the handle portion 22 is about 1 cm long and about 0.5 mm in diameter. The probe portion 24 is about 1 cm long and has a larger diameter than the handle portion, being about 1 mm in diameter. The dilator 20 tapers to a sharp point at the very end of the probe portion for piercing and penetrating tissue, over about the last 0.25 cm of the dilator.

Most importantly, because the handle portion 22 of the dilator 20 has a smaller outer dimension that the probe portion 24, a cavity which is large enough to accept a hair graft is formed when the dilator is inserted into the scalp, and yet a sufficient distance between the handles exists to allow the surgeon to grasp them and work between them.

FIGS. 1–3 illustrate, in overview form, use of a single dilator 20 to facilitate hair graft 26 insertion. First, the dilator 20 is pressed downwardly into the scalp 28 into the galeal layer 30. Penetration of the scalp 28 is facilitated by the tapered end of the dilator 20.

Once inserted into the tissue of a patient, the enlarged probe portion 24 expands the surrounding tissue, as illustrated in FIG. 2. After insertion, the surgeon removes the dilator 20 as illustrated in FIG. 3, leaving a cavity into which the surgeon inserts the hair graft 26. The resiliency of the tissue ultimately causes the tissue around the hair graft 26 to close, securing the graft in place.

FIG. 4 illustrates a manually operated device for use in placing multiple dilators 20 in accordance with a first method of the present invention. In accordance with this method, by manual effort, a surgeon simultaneously places a number of dilators 20 in a predetermined arrangement. The device for accomplishing the method is a cartridge 32 which comprises outer support means in the form of a housing 34 having the form of a contiguous upright wall, a dilator guide 36, and a depressor 38 (see FIGS. 5A and 5B).

The housing 34 of the cartridge 32 is preferably square or rectangular in shape. The particular size, in inner dimension and thickness, varies on the number of dilators to be placed and their size. When four-sided, the housing 34 has a first side 56, a second side 58, a third side 60, a fourth side 62, and an open top end 39 and bottom end 40.

Preferably, the first, second and third sides 56, 58, 60 are rigidly connected, forming a "C"-shaped member. The fourth side 62 is movably or removably connected to the other sides. In particular, the edges of the first and second sides 56,58 which engage the fourth side 62 include a "C"-shaped channel. The fourth side 62 has inwardly facing tabs 64, 66 (66 not visible) on opposing edges which slide in the channels of the first and second sides 56, 58. The fourth side 62, as illustrated in FIG. 4, is thus detachably connected to the first and second sides 56, 58.

Preferably, a stop 68 in the form of a solid member covering the top end of the channels 64, 66, limits downward movement of the fourth side 62 on the first and second sides 56, 56. When connected to the first and second sides, the fourth side completes the contiguous wall comprising the housing 34.

Each of the sides is made of plastic, or a similar durable and sterilizable material. When made of plastic, the first, second, and third sides 56, 58, 60 can be molded as a single piece.

Dilator guide means in the form of a guide or template 36 are located in the cartridge, recessed a short distance up from a bottom edge 41 of the housing 34 on the interior thereof. The particular recess distance is chosen so that when the cartridge 32 is placed on the scalp, the tips of the dilators 20 located in the cartridge 32 are proximate the scalp, as illustrated in FIG. 5a.

The dilator guide 36 is a rectangular member having first and second ends or sides which engage a first groove 44 in the first side 56 of the wall 34, and a second groove 46 in the opposite second side 58 of the wall. The grooves 44, 46 are recessed areas in each of these two sides 56, 58 having approximately the same height as the thickness of the guide. The engagement of the guide 36 with the grooves 44, 46 supports the guide in the housing 34 above the bottom end thereof.

The guide 36 is preferably made of a slightly flexible material, such as rubber, and includes a plurality of passages 42 therethrough. As illustrated in FIG. 4, the passages pass through the guide 36 at about a 30 degree angle with respect to vertical. The passages 42 can be arranged in a variety of patterns, depending on the particular dilator placement pattern desired.

Each passage 42 is sized to accept a dilator. When the dilators 20 have the shape described above, the passage 42 is circular in shape, having approximately the same diameter as the larger probe portion of the dilator 20.

Stop means retain the dilators in the guide 36 in a first position. Preferably, the stop means comprises friction between the dilators and the guide 36. In particular, the size of the passage 42 and the type of material from which the guide 36 is selected so that a dilator 20 placed in a passage is retained therein unless pushed through by an outside force. As illustrated in FIG. 4, the passage size varies when the dilator size varies, such that an individual cartridge can contain a guide having passages of differing sizes.

The depressor 38 is located near the top end 39 of the housing 34, and has a top surface 48, bottom surface 50, and two opposing edges each having an outwardly extending tab 52a,b thereon. The top surface 48 is preferably flat and smooth for engagement with the thumb 49 or finger of a surgeon. The bottom surface 50 is "stepped" providing a number of individual surfaces arranged parallel to the end of each dilator.

The tabs 52a,b are thin members extending outwardly along opposite edges of the depressor. The tabs 52a,b each engage a corresponding ledge 54a,b on the first and second sides 56, 58 of the housing, acting as means for supporting the depressor 38 above or at the ends of the dilators 20 in a first raised position. When a surgeon presses upon the depressor, however, the tabs 52a,b break off, allowing the depressor 38 to move downwardly within the wall 34 of the cartridge 32.

In the first method, a surgeon uses the cartridge 32 of the present invention to simultaneously place a number of dilators 20. First, the surgeon lifts the fourth side 62 upwardly, exposing the interior portion of the cartridge 32. The surgeon presses a dilator guide 36 into the cartridge, the particular guide chosen to have the desired dilator insertion pattern required for that portion of the scalp in which hair grafts are to be inserted.

FIG. 6 illustrates in overview schematic form how hair grafts 26 of different sizes are placed in differing regions of the scalp. Along the normal hair line, many small grafts are inserted. In the central or interior portion of the scalp, larger hair grafts are inserted. Thus, not only does the "density" of the dilators being placed need to vary, but their size often must vary as well.

Once a guide 36 having the desired dilator pattern (in both size and density) is chosen, it is inserted into the cartridge, and the fourth side 62 is pressed downwardly. When relocating the fourth side, the channels 64, 66 slide along and engage the edges of the first and second sides 56, 58, until the stops 68 prevent further downward movement of the side.

Preferably, the appropriately sized dilators 20 are already inserted into the passages 42 in the guide 36 when the guide is inserted. If not, the surgeon inserts dilators into the passages 42.

The surgeon then places the cartridge 32 on the scalp in the desired position, as illustrated in FIG. 5a. In this position, the dilators 20 are located proximate the scalp. The surgeon then presses downwardly on the depressor 38. Pressure on the depressor breaks off the tabs 52a,b on the edges of the depressor, allowing the depressor to slip downwardly past the ledges 54a,b on the first and second sides 56, 58 of the wall 34.

The depressor, which engages the handle portions 22 of the dilators 20, presses them downwardly into the scalp. Eventually, further movement of the depressor 38 is prevented by its contact with the guide, as illustrated in FIG. 5b.

The cartridge 32 is then removed, leaving the dilators in place in the scalp. The cartridge 32 is easily removed without disrupting the dilators 20 because the dilators no longer engage the guide because the small diameter handle portion 22 of each dilator 20 is all that remains in the larger passages 42 of the guide. Then, as illustrated in FIGS. 2 and 3, the surgeon removes the dilators and inserts hair grafts 26 in their place, completing the transplant process.

Preferably, the range of movement of the depressor 38 against the dilators 20 equals the distance the dilators 20 must be pressed into the scalp for optimum hair graft insertion. In the case where the dilators 20 initially just contact the tissue when the cartridge is set on the patient, this distance is normally about 1-2 cm. Thus, the depressor's 38 range of movement against the dilators is about 1-2 cm.

The cartridge 32 of the present invention is reusable. In particular, the surgeon removes the old used depressor 38 from the cartridge and replaces it with a new one having intact tabs 52a,b. When a new depressor 38 is installed, it is again supported by the tabs 52a,b the ledges 54a,b in a raised position.

The surgeon then either inserts new dilators 20 into the passages 42 of the guide, or replaces the guide 36 in the cartridge with a different one if a different dilator insertion pattern is desired.

The above description represents a preferred embodiment of the present invention. However, many variations to the method and device are possible without deviating from the scope of the invention.

For example, the cartridge 32 can have any of a variety of shapes and sizes. Further, the guides can have a variety of sized and spaced dilator accepting passages.

As a further aspect of the present invention, the guide may actually comprise a number of individual elements which are arranged together to form a single grid or element in the cartridge. In this fashion, the guide may be "customized" using only a few guides having fixed patterns. For example, the guides may comprise elongate members having a single row of passages therein, such that when a number of guides are placed together, a grid having numerous rows of differently spaced and sized passages results.

While it is desirable that the passages be pre-formed in the guide, the guide may be made of a pliable material, whereby the surgeon can form the passages simply by pressing dilators into the guide in any desired pattern.

Further, while the passages in which the dilators are located are shown in FIGS. 4, 5a, and 5b as being tilted at a 30 degree angle with respect to the horizontal, the passages can have any orientation. For example, and as illustrated in FIG. 9, the passages can pass vertically through the guide. Alternatively, the passages can pass at an angle of 5, 10, or 45 or more degrees through the guide. When the angle at which the passages pass through the guide is different, the bottom surface 50 of the depressor is reconfigured so that the depressor engages each dilator at a right angle.

As described above, preferably the depressor engages the distal end 22 of the dilators 20 at a right angle. In an alternate form of the present invention, the depressor moves parallel to the direction of dilator movement through the guide. In particular, the depressor may be located on a track in the housing by which the depressor moves downwardly against the dilators at the same angle as the dilators extend through the guide.

A variety of means for selectively attaching the guides to the cartridge other than the engagement with the grooves described above are available. For example, the guide may snap into place or be press-fit into the housing, be held in place by spring-loaded pins which pass through the cartridge wall into the guide, or simply be supported by a ledge extending inwardly from the wall. Also, a variety of means for selectively attaching and detaching the fourth side to access the guides are possible.

Also, the guide may actually comprise a portion of the housing instead of a separate element. For example, the guide may comprise a molded section of plastic having passages or the like therethrough which is directly a part of the outer wall.

As described above, the stop means preferably comprises friction between the dilators and the guide. In this form of the invention, the guide is preferably constructed of rubber or a similar "stretchable" and high-friction material. The guide, however, may be constructed of plastic or a similar rigid material, with each passage lined with rubber or a similar material.

Also, the stop means for retaining the dilators in the template may comprise something other than the friction between the dilators and the guide. For example, a thin pierceable member such as a plastic sheet may be located over the open end of the housing. Alternatively, a removable panel may be located across the open end of the housing, the panel removed when the housing is placed on the scalp, thereby allowing the dilators to be pressed into the scalp.

A second form of the present invention is illustrated in FIG. 7. FIG. 7 illustrates a cartridge 100 for use with an automated gun 101 or other remote automatic triggering or firing device of the type commonly used and found in hospitals and medical offices. Such mechanisms are commonly used to place items such as tissue staples.

In general, the cartridge 100 comprises a tubular housing 102 rotatably connected to a base 104. An actuator 106 passes through the base 104 and into the housing 102 for pressing a dilator 20 therein out of the housing and into the scalp of a patient.

The housing 100 is cylindrical in shape, having a first end 108 and second end 110. The first end of the housing 108 is enclosed, while the second end 110 is open.

The housing 100 is hollow, except for a number of tubes or passages 112 extending inwardly from the first end 108. Each tube 112 has a diameter slightly greater than that of a dilator, and having a slightly longer length. Preferably, the tubes 112 are spacedly located about the outer periphery of the housing 102, and are open at both ends.

An axle 114 passes from the first end of the housing 102 to the base 104. The axle 114 passes along the centerline of the housing 102, allowing the housing 102 to rotate.

The base 104 has a first end 116 for mating engagement with the second end of the housing 102. The first end 116 of the base is thus circular in shape, comprising an outer wall and inner hollow interior space.

The base 104 includes a second end 118 which is adapted for mating engagement with a triggering device or gun 101. In the embodiment illustrated, the second end 118 has a generally rectangular shape.

An aperture 120 is located in one surface of the second end 118 of the base 104, forming a passage into the interior of the base. The actuator 106 is generally "L"-shaped, extending from the aperture through the base and into the housing 102. A first end of the actuator 106 extends upwardly to the aperture 120 for engagement by a trigger mechanism in the gun 101. A second end of the actuator 106 is located adjacent the end of one of the tubes 112.

Stop means releasably retain the dilators 20 in the tubes 112. The stop means preferably comprises friction caused by a slight interference fit between the dilator and the housing.

In use, a dilator 20 is placed in each of the tubes 112, with the tapered point facing outwardly. The base 104 of the cartridge 100 is located in a gun 101, and one of the tubes 112 is aligned with the second end of the actuator 106.

The surgeon actuates the gun 101, moving the actuator 106 towards the first end of the housing. The second end of the actuator 106 engages the end of the dilator 20 in the aligned tube, pressing the dilator through the tube and into the scalp. The surgeon lifts the gun 101 upwardly so that the housing 102 clears the end of the dilator, and proceeds to place the next dilator.

A surgeon places the next dilator by rotating the housing 102 with respect to the base 104, until the second end of the actuator 106 is aligned with another tube containing a dilator. The gun is again triggered, with the next dilator forced into the scalp.

In this form of the invention, the tube 112 holding the dilator 20 is located close to the outer edge of the housing 102, so that the next dilator can be placed very close to the last. Further, the range of movement of the actuator 106 is chosen so that the dilator 20 is pressed the appropriate distance into the scalp.

In this embodiment, the stop means may comprise a separate element such as a rubbery gasket through which the dilator extends, or a membrane or plate extending across the open end of the tubes which is either pierceable or movable when the dilators are depressed into the scalp.

Figure 8:
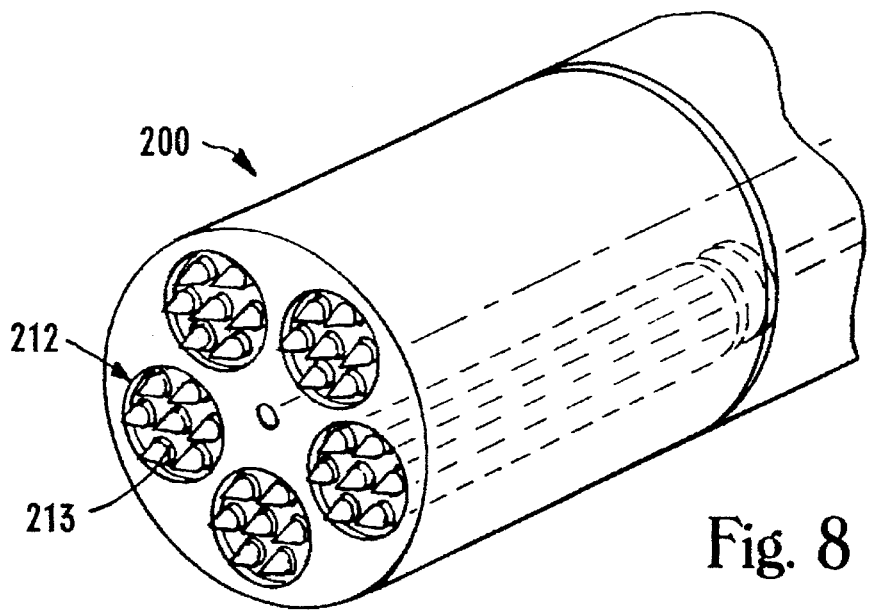
FIG. 8 is a perspective view of a third embodiment of the present invention, illustrating an automated rotating multiple shot dilator cartridge.

Further, the tubes or passages in which the dilators are located can be arranged in a variety of configurations. A third embodiment device of the present is illustrated in FIG. 8. In this embodiment, several dilators are placed in the scalp automatically when a surgeon operates a gun.

In particular, this cartridge 200 is nearly identical to that described above, except the tubes 212 in a housing 202 thereof are configured to receive multiple dilators 20. In the embodiment illustrated, each tube 212 is sized to receive seven dilators. The tube 212 thus includes eight distinct tubes or conduits 213, each of which holds a single dilator. Again, each end of each tube 212, and each passage 213 therein, is open.

In use, when a surgeon actuates the gun or automated firing device, the actuator presses all of the dilators in a tube 212 into the scalp. In the configuration illustrated, all eight dilators in the passages in a single tube are pressed into the scalp.

It is possible to have a wide variety of numbers of tubes and passages therein, for placing a different number of dilators. Further, the passages can be arranged in a wide variety of configurations, whereby the multiple dilators are placed in the scalp in a specific configuration.

FIG. 9 illustrates a fourth embodiment device of the present invention. In particular, this variation of the device is similar to that illustrated in FIG. 4, except that it is automated.

In this form of the invention, a cartridge 300 includes a housing 302 with a first bottom open end 304 and second gun-engaging end 306. A dilator guide 308 and depressor 310 are located inside of the housing 302.

The second end 306 of the housing 302 is shaped for engagement with the end of a triggering device, such as a spring-loaded or air-powered gun. In the form illustrated, the second end 306 is an elongate, somewhat rectangular shaped member.

The remainder of the housing 302 is box-shaped, except that the first end 304 is open. Similar to the cartridge 32 illustrated in FIGS. 4, 5a, and 5b, a removable dilator guide 308 is located within the housing, recessed a short distance from the open first end 304.

Preferably, a surgeon can open and close one side of the housing 302 to access the guide 308, similar to the manner described above in the first embodiment.

The depressor 310 is located between the guide 308 (at the end of the dilators therein) and the second end 306 of the housing 302. The depressor 310 has a perimeter shape which matches the inside shape of the housing 302, to be freely moveable between a first retracted position and a second depressed position.

A bottom surface 312 of the depressor 310 is adapted to press on the dilators at a right angle, as discussed above in more detail. Preferably, the depressor 310 is connected to an actuator 316 which extends into the second end 306 of the housing for engagement with the gun.

Means for biasing the depressor 310 in the form of a pair of springs 318, 320 maintain the depressor 310 in a normally retracted position. The springs 318, 320 are chosen so that upon firing of the gun, the actuator 316 moves against the spring force, pressing the actuator downwardly against the dilators.

In use, a surgeon inserts a loaded dilator guide 308 into the housing 302 of the cartridge. Once loaded, the surgeon inserts the cartridge 300 into a gun. The surgeon then places the open end 304 of the cartridge 300 against the scalp of a patient in the desired location.

The surgeon triggers the gun, effectuating movement of the actuator 316 and pressing the depressor downwardly against the dilators and the opposing spring force. The dilators are pressed through the passages in the guide 308 and into the scalp. Once the dilators are placed, the springs 318, 320 bias the depressor back upwardly to the retracted state, when a new loaded dilator guide can be inserted into the cartridge.

In accordance with this method, numerous dilators are simultaneously placed into the scalp using an automated machine. Once again, the particular location of the dilators is effectuated by choosing a guide having a specific configuration of dilator-holding conduits.

Figure 10:
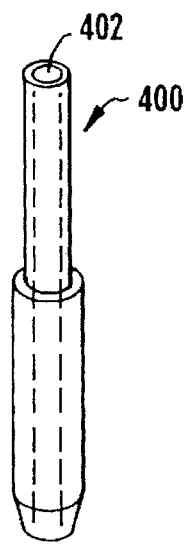
FIG. 10 illustrates a second form of dilator for use in the methods and devices of the present invention.

While it is preferred that the dilator illustrated in FIGS. 1-3 be used in the methods and devices of the present invention, other configurations of dilators can be used. For example, FIG. 10 illustrates a second form of dilator 400 for use in the methods and apparatus of the present invention. The dilator 400 is similar to that described above, except that it has a hollow passageway 402 along the centerline thereof. This dilator 400 has the effect of coring a section of tissue from the patient when the dilator is inserted and then removed.

FIGS. 11-13 illustrate a fifth embodiment of the present invention. In this embodiment of the present invention, the device for simultaneously placing dilators are interengaging templates, with the dilators comprising a series of spikes on one of the templates. In particular, a first or female template 500 comprises a thin base member 502 having a top surface 504 and a bottom surface 506. A number of cylindrically shaped guides 508 depend downwardly from the bottom surface 506 of the template, each having a tapered or bevelled distal end 509. Each guide 508 has a length nearly equal to the depth the hair grafts must be placed into the tissue of the patient to maximize graft survival.

A passage 510 extends through the top surface 504 of the template down through each of the guides 508. The location of each of the guides 508 on the template 500 matches the spacing of later to be placed hair grafts 532.

A second or male template 512 comprises a thin base member 514 having a top surface 516 and bottom surface 518. A number of spikes or probes 520 extend downwardly from the bottom surface 518 of the template.

Preferably, the spikes 520 are longer than the passages 510 through the female template 500, and have a smaller outside diameter than the diameter of the passages 510 through the guides 508 and passages through the guides of a third template described below. The spikes 520 have a distal end which tapers to a point. The spikes 520 are arranged in the same pattern as the guides 508 on the female template.

As illustrated in FIG. 13, a third template 522 comprises a base plate 523 having a top surface 524 and bottom surface 526. A number of cylindrical guides 528 depend downwardly from the bottom surface 526 of the template. A passage 530 extends through the template 522 and each of the guides 528. Preferably, the outer dimension of each of the guides 528 is smaller than the size of the passage 510 of the female template 500. The guides 508 are arranged in the same pattern as the guides 508 in the female template 550, for mating engagement therewith.

In use, as illustrated in FIGS. 12 and 13, a surgeon presses the male template 512 into the female template 500. In particular, the surgeon aligns the spikes 520 of the male template with the passages 510 through the guides 508 in the female template 500. The surgeon presses the two templates 500, 512 together until the bottom surface 518 of the male template 512 engages the top surface 504 of the female template. When engaging one another, the spikes 520 and guides 508 form "dilators" for placement in the tissue 534 of the patient. The surgeon places the combination on the scalp of the patient and presses downwardly until the bottom surface 506 of the female template 500 contacts the scalp, preventing further movement. The surgeon then pulls the male template 512 from the female template 500, leaving the female template in place.

When the female template 500 is in place, the passages 510 therethrough form cavities in the tissue of the patient into which hair grafts 532 may be inserted. In particular, the surgeon or an assistant places hair grafts 532 into each of the passages 530 of the third template 522, and then the surgeon presses the third template into engagement with the female template 500 which is engaging the patient.

When the surgeon presses the third template 522 into the female template 500, each hair graft 532 is effectively positioned in the tissue of the patient. Preferably, the surgeon then presses the male template 512 into the other two templates, whereby the spikes 520 engage the hair grafts 532 and push them into the bottom of the formed cavities. The surgeon then removes all of the templates, leaving the hair grafts 532 in place in the tissue of the patient.

In the above-described device, the templates may comprise substantially rigid members made of plastic or similar material. Preferably, however, so that the device can conform to the varying shape of the patient, the base of each template is constructed of a slightly flexible material, such as a rubber or flexible plastic. The spikes and guides, however, are preferably constructed of a rigid material which easily penetrates tissue.

Further, the size and location of the guides and corresponding spikes may vary. For example, the guides and spikes may be located on their respective bases in a variety of patterns for use in positioning hair grafts in the same variety of patterns on the scalp. Also, the guides, and thus the matching spikes, may vary in size, both on different templates, and even on the same template, depending on the size of hair graft to be implanted.

It will be understood that the above-described arrangements of apparatus and the method therefrom are merely illustrative of applications of the principles of this invention and many other embodiments and modifications may be made without departing from the spirit and scope of the invention as defined in the claims.

I claim:

1. A device for implanting a plurality of individual dilators into the tissue of a patient, each dilator, when removed defining a cavity to receive a graft, the device comprising:
   a housing;
   guide means located in said housing, said guide means comprising a plurality of passageways for receiving a plurality of dilators therein;
   releasable stop means for releasably retaining each of the dilators mounted in the guide means in a fixed position in the housing; and
   depressor means for simultaneously urging the dilators through the passageways and from said guide means to each be implanted into the tissue to dilate the same.

2. The device of claim 1, wherein said guide means comprises a template having a pre-determined pattern of passageways.

3. The device of claim 1, wherein said stop means comprises friction between said dilators and said guide means.

4. The device of claim 1, wherein said housing comprises an upstanding wall.

5. The device of claim 1, wherein said housing is a wall having four sides, one of said four sides movable with respect to the remaining sides.

6. The device of claim 1, wherein said depressor means comprises a plate.

7. The device of claim 6, wherein said depressor includes first and second outwardly extending tabs, and said housing includes first and second ledges, said depressor retained in a first raised position when said tabs engage said ledges.

8. The device of claim 1, wherein said housing includes first and second grooves located on an inner surface, and said guide means comprises a template, said template removably supported on an inner surface of said housing by engagement with said grooves.

9. The device of claim 1, wherein said depressor means comprises a plunger connected to actuating means.

10. The device of claim 1, wherein said housing is cylindrical in shape.

11. The device of claim 1, further including a base member, said housing rotatably connected to said base.

12. The device of claim 11, wherein said base is adapted for engagement with a remote actuating device.

13. The device of claim 1, wherein said guide means comprise tubes located in said housing.

14. A method of simultaneously implanting a plurality of individual dilators into the tissue of the patient, each implanted dilator adapted to dilate the tissue to receive a graft, the method comprising;
   releasably retaining said dilators in a guide means;
   locating said guide means proximate said tissue;
   pressing and releasing said dilators from said guide means into said tissue to implant the dilators in the tissue to dilate the same; and
   removing said guide means leaving the dilators implanted in the tissue.

15. The method of claim 14, wherein said releasably retaining step comprises locating said dilators in passages in said guide means.

16. The method of claim 14, wherein said pressing step comprises forcing a depressor downwardly against a first end of each of said dilators.

17. The method of claim 14, additionally comprising the step of inserting said guide means into a housing.

18. The method of claim 14, wherein said pressing step additionally comprises the step of triggering an actuating mechanism.

19. The method of claim 14, wherein said guide means comprises a template, and additionally comprising the step of selecting a template having a plurality of passage therein in a predetermined pattern, whereby said dilators are implanted in said tissue in a predetermined pattern.

20. The method of claim 14, further including the step of selecting a pattern for insertion of hair grafts into the tissue of said patient, and wherein said retaining step comprises retaining said dilators in said selected pattern.

21. In combination, an apparatus for placing a plurality of individual dilators in tissue of a patient, each dilator adapted to displace tissue to form a cavity to retaining said dilators in a plurality of passages therein, stop means for releasably retaining said dilators in said guide means, and means for urging said dilators from said guide means to be placed into the tissue of the patient and to be released from the guide means.

22. The combination of claim 21, wherein said dilators comprise elongate members having a first handle portion and a second probe portion, and wherein said second probe portion tapers to a pointed end.

23. The combination of claim 21, wherein said dilators comprise elongate members having a first blunt end, and a passage therethrough.

24. The combination of claim 21, wherein said guide means comprises a template removably located in said housing.

25. The combination of claim 21, wherein said means for depressing comprises plate located on said housing in a first raised position and movable to a second depressed position.

26. A device for forming cavities in the tissue of a patient into which a hair graft may be positioned, comprising:
   a first template comprising a base member having a plurality of downwardly extending guide means having passages therethrough;
   a second template comprising a base member having a plurality of downwardly extending spikes adapted to be received into said passages to define with said guide means a plurality of dilators to be inserted into the tissue to form said cavities, removal of said second template spikes from the passages providing for placement of said grafts through said passages into said cavities.

27. The device of claim 26, wherein said guides in said first template are cylindrical in shape and said spikes on said second template have a distal end which tapers to a point adapted to penetrate the tissue.

28. The device of claim 26, further including a third template comprising a base member having a plurality of downwardly extending guide members having passages therethrough to receive grafts, said guide members adapted to be received by said passages of the first template.

29. A method of locating a plurality of hair grafts in the tissue of a patient, comprising:

locating a plurality of spikes extending downwardly from a base member of a first template into a plurality of hollow guide members extending downwardly from a base member of a second template;

pressing said spikes in said guide members into the tissue of the patient;

removing said first template from said second template;

placing a plurality of hair grafts into the plurality of guide members of said second template; and removing said second template from the tissue of the patient.

30. The method of claim 29, wherein said placing of said hair grafts comprises the steps of placing hair grafts into guides in a third template and pressing said guides of said third template into a plurality of guides of said second template.

31. The method of claim 30, further including the step of pressing said spikes of said first template into the guides of said third template.

32. A device for implanting a plurality of dilators into the tissue of a patient, comprising:

a housing with a wall having four sides, one of said four sides moveable with respect to the remaining sides;

guide means located in said housing, said guide means comprising a plurality of passageways for retaining a plurality of dilators therein;

releasable stop means for retaining dilators mounted in the guide means in a fixed position in the housing; and depressor means for simultaneously urging the dilators through the passageways in said guide means.

33. A device for implanting a plurality of dilators into the tissue of a patient, comprising:

a housing;

guide means located in said housing, said guide means comprising a plurality of passageways for retaining a plurality of dilators therein;

releasable stop means for retaining dilators mounted in the guide means in a fixed position in the housing; and depressor means for simultaneously urging the dilators through the passageways in said guide means, said depressor means comprising a plate having first and second outwardly extending tabs, and said housing includes first and second ledges, said depressor retained in a first raised position when said tabs engage said ledges.

34. A device for implanting a plurality of dilators into the tissue of a patient, comprising:

a housing having first and second grooves located on an inner surface, and said guide means comprises;

guide means located in said housing comprising, a template, said template removably supported on an inner surface of said housing by engagement with said grooves, said template having a plurality of passageways for retaining a plurality of dilators therein;

releasable stop means for retaining dilators mounted in the guide means in a fixed position in the housing; and depressor means for simultaneously urging the dilators through the passageways in said guide means.

35. A device for implanting a plurality of dilators into the tissue of a patient, comprising:

a base member;

a housing rotatably connected to said base;

guide means located in said housing, said guide means comprising a plurality of passageways for retaining a plurality of dilators therein;

releasable stop means for retaining dilators mounted in the guide means in a fixed position in the housing; and depressor means for simultaneously urging the dilators through the passageways in said guide means.

36. A method of simultaneously implanting a plurality of dilators into the tissue of the patient comprising;

selecting a template having a plurality of passages therein in a predetermined pattern;

retaining a plurality of dilators in said template passages;

locating said template proximate said tissue;

pressing said dilators from said template into said tissue; and removing said template from said tissue.

37. A method of simultaneously implanting a plurality of dilators into the tissue of the patient comprising;

selecting a pattern for insertion of hair grafts into the tissue;

retaining a plurality of dilators in a guide means in said selected pattern;

locating said guide means proximate said tissue;

pressing said dilators from said guide means into said tissue; and removing said guide means.

38. In combination, an apparatus for placing a plurality of dilators in tissue of a patient comprising a housing having a template removably located in said housing for releasably retaining said dilators in a plurality of passages therein, stop means for releasably retaining said dilators in said template passages and means for depressing said dilators from said template into the tissue of the patient.

39. A device for forming cavities in the tissue of a patient into which a hair graft may be positioned, comprising:

a first template comprising a base member having a plurality of downwardly extending guide means having passages therethrough;

a second template comprising a base member having a plurality of downwardly extending spikes for positioning in said passages through said guide members in said first template; and a third template comprising a base member having a plurality of downwardly extending guide members having passages therethrough.

* * * * *